United States Patent [19]
Pennig et al.

[11] Patent Number: 5,681,318
[45] Date of Patent: Oct. 28, 1997

[54] MEDULLARY CAVITY TEMPLATE

[75] Inventors: Dietmar Pennig, Cologne, Germany; Giovanni Faccioli, Monzambano; Stefano Rossi, Verona, both of Italy

[73] Assignee: Orthofix S.r.l., Bussolengo, Italy

[21] Appl. No.: 318,671

[22] Filed: Oct. 12, 1994

Related U.S. Application Data

[63] Continuation-in-part of Ser. No. 135,155, filed as PCT/DE97/00134, Feb. 11, 1993, abandoned.

[30] Foreign Application Priority Data

| Feb. 13, 1992 | [DE] | Germany | 9201811 U |
| Feb. 20, 1992 | [DE] | Germany | 9202174 |
| Oct. 12, 1993 | [IT] | Italy | VR93A0074 |

[51] Int. Cl.[6] ............................................. A61B 17/56
[52] U.S. Cl. ........................... 606/98; 606/96; 606/86
[58] Field of Search ............................ 606/102, 96, 97, 606/98, 86, 62, 63, 64, 95, 99

[56] References Cited

U.S. PATENT DOCUMENTS

| 4,337,773 | 7/1982 | Raftopoulos | 606/95 |
| 4,733,654 | 3/1988 | Marino . | |
| 4,800,873 | 1/1989 | Audell . | |
| 4,844,064 | 7/1989 | Thimsen et al. | 606/80 |
| 4,865,025 | 9/1989 | Buzzi et al. . | |
| 5,122,146 | 6/1992 | Chapman et al. | 606/102 |
| 5,171,248 | 12/1992 | Ellis | 606/102 |
| 5,190,548 | 3/1993 | Davis | 606/80 |
| 5,234,434 | 8/1993 | Gable et al. | 606/96 |

OTHER PUBLICATIONS

Richards Manufacturing Company Brochure "New Hansen–Street Intramedullary Nail for the Femur" 1949, 1 page, Author Unknown.

*Primary Examiner*—Guy V. Tucker
*Attorney, Agent, or Firm*—Hopgood, Calimafde, Kalil & Judlowe

[57] ABSTRACT

A medullary cavity template has a tubular body adapted to the shape of a medullary nail. The tubular body has one or more x-ray viewable discontinuities in the region of its distal end. The tubular body also has a scale in the region of its proximal end, the scale being on the outside of the body for external viewing to measure axial depth of a medullary cavity.

6 Claims, 3 Drawing Sheets

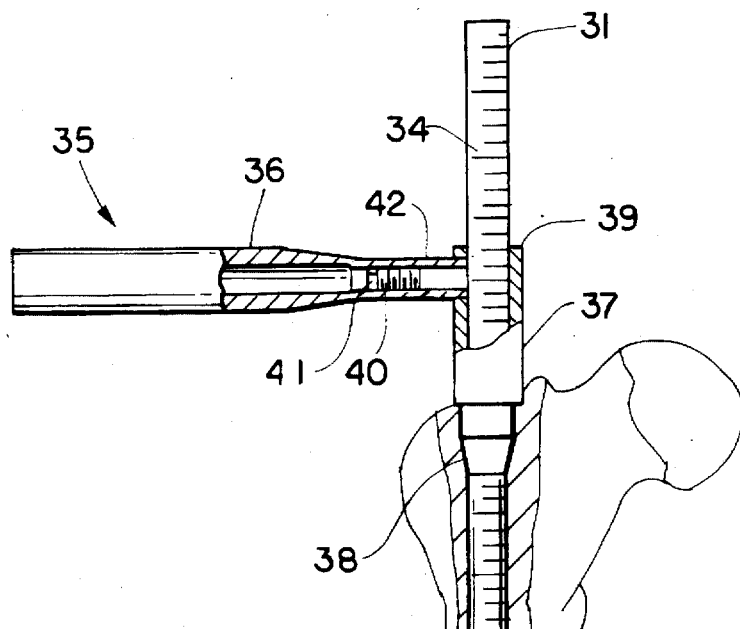
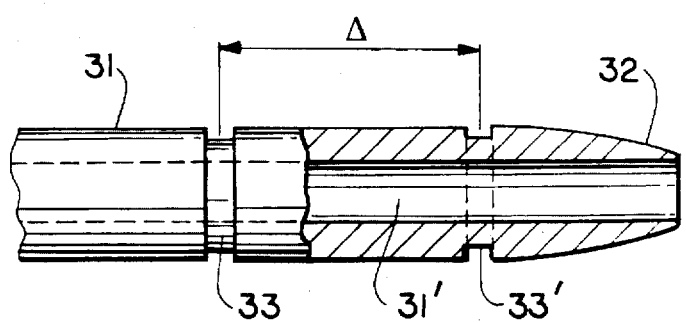
FIG.6
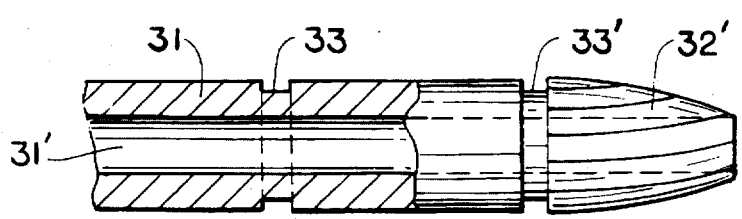
FIG.7
FIG.5
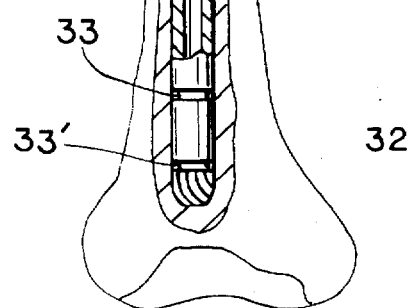

MEDULLARY CAVITY TEMPLATE

RELATED CASE

This application is a Continuation-in-Part of U.S. patent application Ser. No. 08/135,155, filed as PCT/DE97/00134, Feb. 11, 1993, now abandoned.

BACKGROUND OF THE INVENTION

The present invention relates to a medullary cavity template for removable insertion in a drilled medullary canal.

Before inserted implantation of a medullary nail, a bone to be treated is customarily drilled to permit an easy introduction of the nail. It is of great importance to avoid forcefully hammering the nail into implanted position, since hammer blows can cause severe health problems.

It is also difficult in many cases to determine the correctly implanted position of a medullary nail, and it therefore happens time and again that an inserted nail must be removed for replacement by a nail which has a precise length.

It also happens time and again that the nail does not fit perfectly into the drilled medullary canal so that it must be removed, and a new drilling becomes necessary. By this time, the guide wire or guide pin that was used for initial drilling has already been removed, so that this circumstance also results in great difficulties.

BRIEF STATEMENT OF THE INVENTION

It is the object of the invention to provide a template or gauge for removably inserted use in a drilled medullary cavity prior to nail implantation, whereby the above-mentioned disadvantages can be reliably avoided.

The invention achieves this object by providing a template in the form of an elongate tubular body which has an outer diameter conforming to a medullary-nail diameter selected for implantation and which has marking indicia along its length whereby to ascertain and select the standard-length medullary nail that is most appropriate for implantation in a particular patent, as well as a means of identifying the location at which to drill the bone with one or more transverse bores for accurate bone-screw (bolt or pin) register with the standard one or more transverse bores of a subsequently implanted medullary nail.

Stated in other words, the invention provides a template or gauge in the form of a hollow body which essentially corresponds in its size and shape to the medullary nail. The body has at its proximal end an actuating handle and at its distal end an opening for piloted guidance along a guide wire or drill pin. In the region of the distal end, x-ray viewable, axially local discontinuities such as apertures or grooves are provided, for example, arcuate slots at diametrically opposed front and rear sides of the hollow body, these apertures or grooves make it possible, under x-ray viewing, to see where transverse bores, if any, are to be drilled in the bone, for reception of attachment screws, bolts or the like in the medullary nail which is to be subsequently implanted. At its proximal end, the outer surface of the tubular body has measurement-scale indicia consistent with the measurement lengths of standardized medullary nails. Thus, after insertion of the tubular body (i.e., of the medullary template), one can now measure the longitudinal extent of the drilled opening along the medullary canal, so that the precise length of required medullary nail can be determined accordingly. Furthermore, upon ascertaining the location of one or more apertures or grooves of the inserted template, one knows where to provide one or more drilled transverse bores to receive one or more bolts for locking the medullary nail in place.

DETAILED DESCRIPTION

Preferred embodiments of the invention will be described in detail with reference to the accompanying drawings, in which:

FIG. 5 is a view in side elevation of a third embodiment;

FIG. 6 is an enlarged fragmentary view in side elevation of the distal end of the third embodiment; and FIG. 7 is a view similar to FIG. 6 to show a modification.

Figure 1:
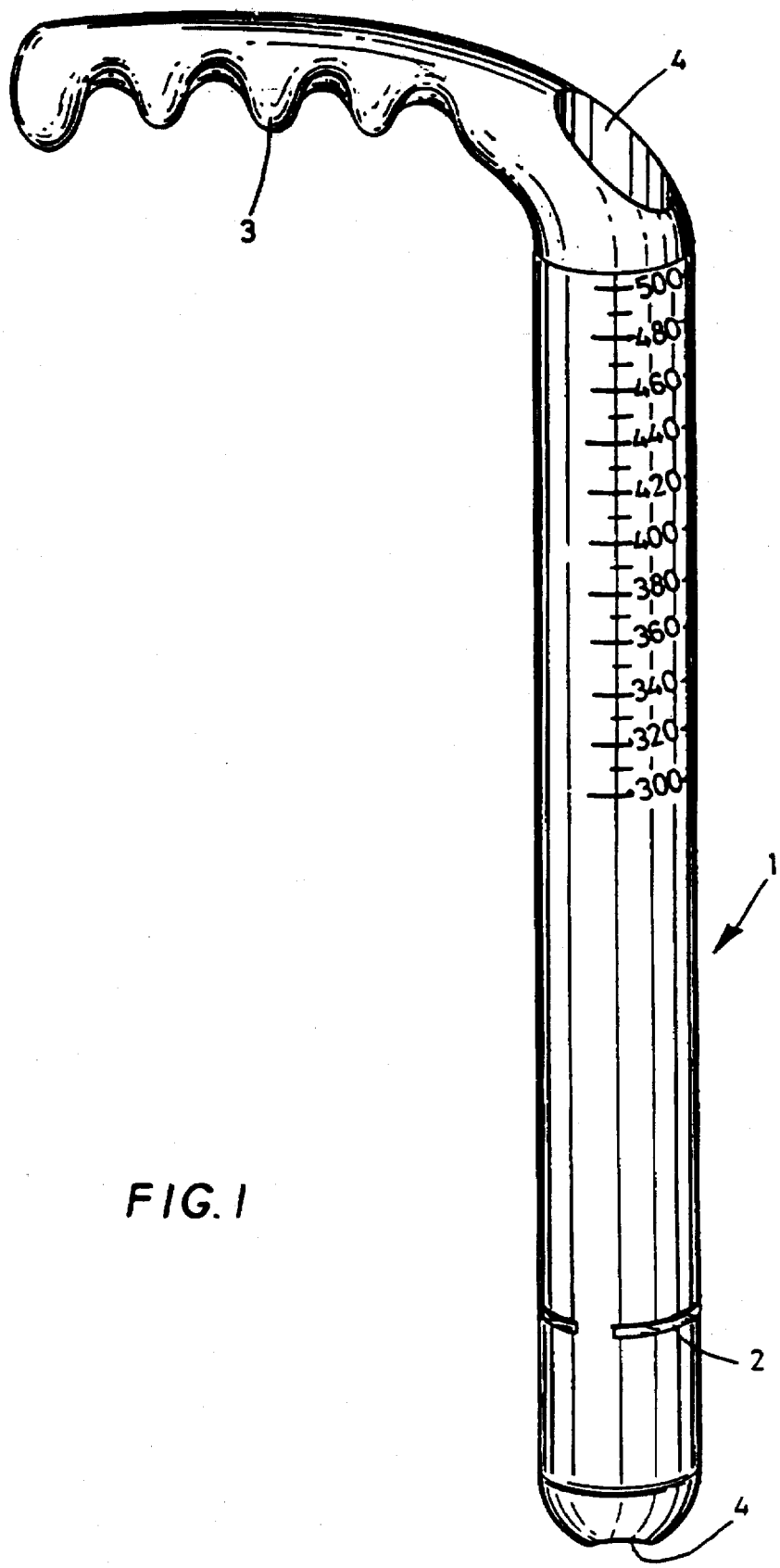
FIG. 1 is a perspective view of a first medullar-template embodiment of the invention.

In FIG. 1, a medullar template of the invention is seen to comprise a hollow body 1 having a fixed or integrally formed handle 3 at its proximal end. A measurement scale is observable along the outer surface of body 1, in the proximal-end region. The hollow body has a continuous bore 4 for a guide wire or drill pin, and this bore is open at its proximal and distal ends. Further, in the distal region, diametrically opposed apertures in the form of slots 2 are provided in front and rear sides of body 1. These slots 2 can be recognized under x-ray viewing, thereby indicating the location at which to drill the bone for registry with the standard transverse hole which is a feature of the medullary nail that is selected for subsequent implantation.

Preferably, the outside diameter of the template shown is equal to or somewhat larger than the outside diameter of a medullary nail, and the wall thickness of the template is about 2.5-mm. The slots 2 provided in the distal region should have a width of about 4-mm. The material of the template is preferably stainless steel.

Figure 2:
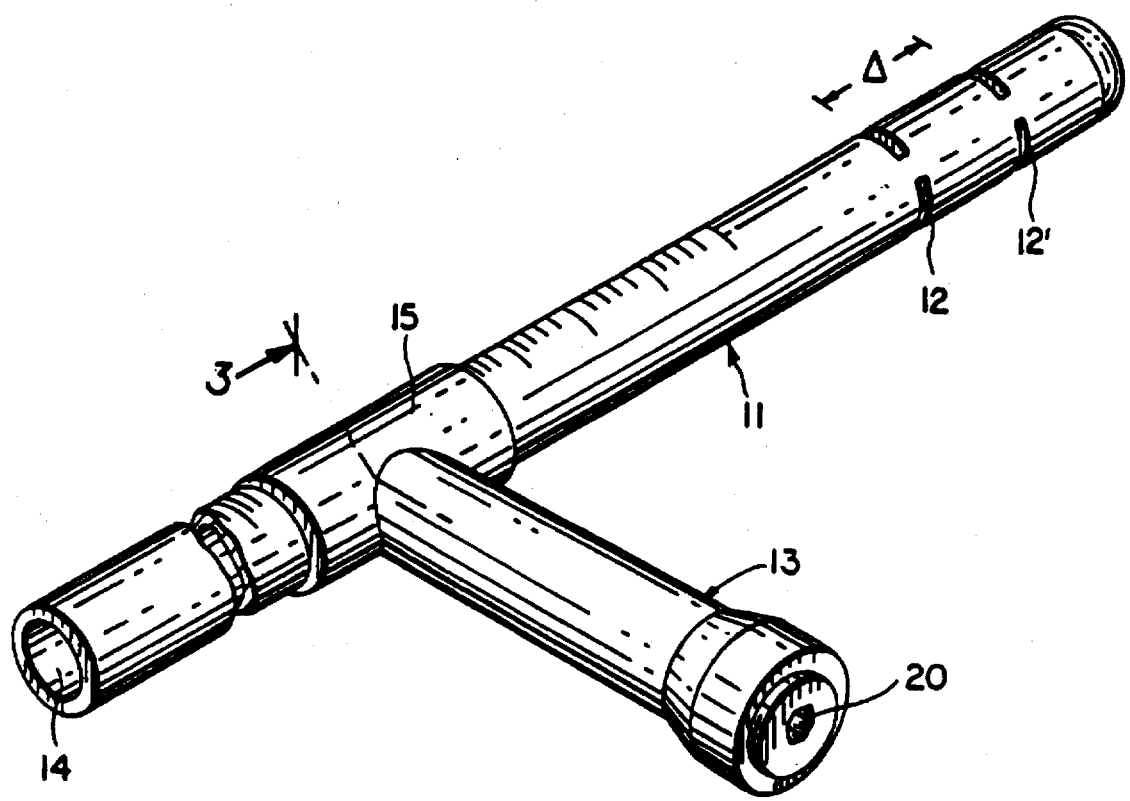
FIG. 2 is a perspective view of a second embodiment.
Figure 3:
FIG. 3 is a sectional view taken at 3—3 of FIG. 2.
Figure 3:
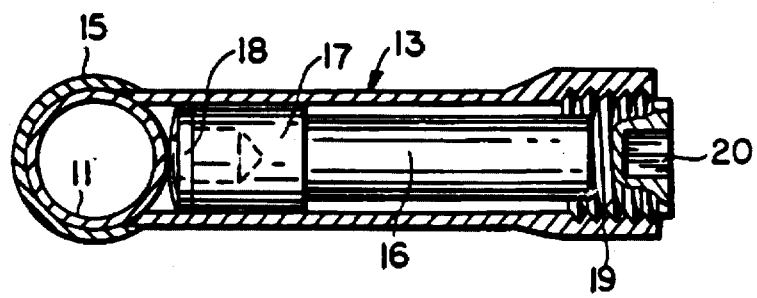

In the embodiment of FIGS. 2 and 3, the medullary template 11 is again an elongate tubular body having a bore 14 which is open at both its proximal and distal ends. And in the region of the distal end, two pairs of slots 12, 12' are seen at a longitudinal spacing Δ which will be understood to duplicate the standard spacing of transverse bores in the medullary nail (or in each nail of a series of medullary nails of differing length) to be selectively served by the template of FIGS. 2 and 3. Again, graduations of a longitudinal-measurement scale are viewable along the more proximal range of offsets from the distal end of the template body. A handle 13 is seen to be tubular and to extend radially from the template body, being fixed at its distal end to a sleeve member 15 that is slidably guided along the template body. As shown, a rod member 16 within handle has an enlarged head 17 at its distal end and mounts a crowned friction element 18, as of elastomeric material, for releasably lockable local engagement with the template body through the sleeve (15) opening via which handle 13 is fitted to the sleeve. A threaded engagement 19, between the proximal end of rod member 16 and the proximal end of the bore of handle 13, is actuable by wrench access to a recess 20 in the proximal end of the rod member, to determine releasably fixed positioning of handle 13 along the template body.

Figure 4:
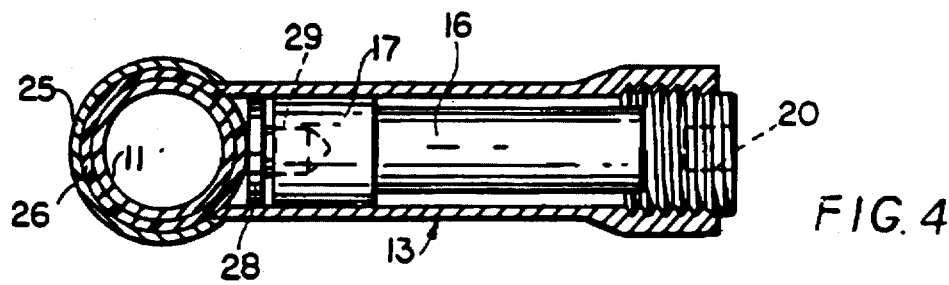
FIG. 4 is a view similar to FIG. 3 to show a modification.

In the modification of FIG. 4, the distal end of handle 13 features a sleeve 25 slidably guided along the template body but with an interposed bushing 26 of plastic material. And the adjustable rod 16 pivotally supports a rigid pressure disc 28, the same being shown with an axial pivot pin to mount the same via a central bore 29 in the distal end of the enlarged head 17 of rod 16. Thus, in FIG. 4, once rod 16 has been advanced in the clamping direction, disc will be operative to apply clamping pressure on the template tube via a local squeeze of the bushing material.

In the embodiment of FIGS. 5 and 6, the x-ray viewable discontinuities 33, 33' near the distal end of the tubular body 31 are circumferential, radially inwardly formed and radially outwardly open grooves, being axially spaced apart to the extent Δ and axially offset from the distal end of body 31, to an extent corresponding to the respective axial offsets of one or more bolt or screw-anchoring apertures of the medullary nail selected for each particular use. Each of the grooves 33, 33' may be of limited circumferentially arcuate extent; but preference is indicated that these grooves shall be circumferentially continuous and that the sidewalls of each groove be defined by and between axially spaced radial planes, wherein the axial spacing is less than the arcuate extent of the groove. For example, for a 12-mm diameter tubular body 31 having a 7-mm bore diameter and 2.5-mm wall thickness, the depth of each groove may suitably be in the range of 0.5 to 1.25-mm, with axial width of 2-mm, for good x-ray viewability.

As shown, body 31 has a continuous bore 31' for a guide wire and an outer diameter corresponding to the outer diameter of a standard medullary nail. At its distal end 32, body 31 is convergently tapered with a rounded, generally ogival contour to the point of intersection with the bore diameter, at which point the angle of intersection between the convergent taper and the bore 31' is in the range of 25 to 35 degrees, as viewed in a longitudinal section. As further seen in the modification of FIG. 7, the convergent distal-end contour may be characterized by sharply defined flutings 32' thus defining small cutting edges. These cutting edges enable the surgeon to use the template as a boring tool, to eliminate slight impediments and/or irregularities in the medullary canal, without having to remove the template for renewed insertion and use of a boring tool.

At the proximal end of the template body 31 of FIG. 5, the handle 35 is again a tubular, being shown with a reduced end 42 that is secured to a sleeve 37 which is slidable along the scale-marked proximal region 34 of body 31. A clamp element 40 has thread engagement with the bore of handle 35 and is manipulated between clamped and released engagement to body 31, via inserted Allen-head tool engagement to its wrench socket 41. Sleeve 37 features a distally convergent frusto-conical distal end 38 of such convergent angle as to permit its insertion, with abutment in the proximal end of the bored hole in the medullary canal, in order to verify whether canal-boring has been sufficient or must be extended. At its proximal end, sleeve 37 has a circumferential rim which enables clear reading of markings of scale 34 to measure length of the bored hole.

In use, after having inserted tubular body 31 into the bored medullary canal with the aid of a guide wire, it can be verified whether the template enters freely or whether it is blocked, as due to an insufficient diameter of the medullary canal. In such case, the distal end 32 of the template cannot completely enter the canal and therefore redrilling is necessary in order to produce a larger diameter.

Once it is determined that the drilled bore in the medullary canal is of correct size for full insertion of the template body 31, the location for distal drilling of bone cortex can be identified and marked, from x-ray viewing of discontinuities 33, 33', and sleeve 37 can be set to its taper fit 38 to the proximal end of the canal bore. At this point, the length of the drilled medullar cavity can be read by noting rim 39 against the scale 34, in order to select a medullary nail of correct length.

For the described template devices, it will be clear that the outside diameter of the tubular template body should be dedicated to a particular selected one of the standard available medullary-nail diameters, e.g., 9-mm, 10-mm, 11-mm, 12-mm. The orthopedic surgeon is thus best served by a kit comprising two or more of the described medullar templates, each of the two or more devices in the kit being dedicated to the particular diameter of the standard medullar nail which he selects (from his available varieties) for installation in his patient. And of course, for each of these different-size medullar templates, the spacing Δ and the axial offsets of slots or grooves from the distal end will be understood to correspond to the spacing and offsets of fixation bolt holes in the medullar nail to be used.

We claim:

1. A medullary cavity template, comprising an axially extending elongate tubular body which substantially conforms to the shape of a medullary nail, said body being of uniform thickness for substantially its entire length and said body having, in the region of its distal end but axially short of its distal end, one or more radially open local slots through said thickness; and said body having, in the region of its proximal end, an externally viewable scale for measuring lengths, said one or more slots being axially spaced from the distal end of said body in accordance with the axial location of apertures in the medullary nail, each of said one or more slots having both an axial extent and a circumferentially arcuate extent, wherein the circumferentially arcuate extent is in excess of the axial extent.

2. A medullary cavity template according to claim 1, having a handle at the proximal end of the tubular body.

3. A medullary cavity template according to claim 2, wherein the handle extends in a radial direction with respect to the tubular body.

4. A medullary cavity template according to claim 1, wherein the tubular body has a wall thickness of about 2.5 mm.

5. A medullary cavity template according to claim 1, wherein the tubular body is open at both ends.

6. A medullary cavity template comprising an axially elongate tubular body substantially conforms to the shape of a medullary nail, said body having an elongate outer cylindrical surface which has in the region of its distal end but actually short of its distal end at least one fully circumferential radially inwardly formed and radially outwardly open groove of axial width that is less than the arcuate extent of said groove, said groove being axially offset from the distal end of the tubular body wherein the axial offset corresponds to the axial offset of a distal aperture in the medullary nail, and said body having in the region of its proximal end, an externally viewable scale for measuring lengths, the medullary cavity template further including a sleeve slidably movable along the tubular body, a tubular handle mounted to said sleeve, and clamp mechanism contained within said handle and selectively operable for releasably securing said sleeve to an adjusted portion along said tubular body wherein said sleeve has a convergent frustoconical distal end.

* * * * *